United States Patent [19]

Kazama

[11] Patent Number: 5,509,890
[45] Date of Patent: Apr. 23, 1996

[54] HEART RETRACTOR

[76] Inventor: Shigeru Kazama, 2-6-3, Naruse, Machida, Tokyo, Japan

[21] Appl. No.: 340,030

[22] Filed: Nov. 14, 1994

[30] Foreign Application Priority Data

Dec. 16, 1993 [JP] Japan .................. 5-075050 U

[51] Int. Cl.$^6$ ........................................ A61F 2/00
[52] U.S. Cl. ................................. 600/37; 600/201
[58] Field of Search ................... 600/37, 201, 206, 600/208; 623/3; 601/132; 602/4,6,60–61, 75–76, 903; 606/151

[56] References Cited

U.S. PATENT DOCUMENTS 3,983,863 10/1976 Sanke et al. ................ 600/37
4,973,300 11/1990 Wright ........................ 600/37

*Primary Examiner*—Angela D. Sykes
*Assistant Examiner*—John P. Acyk
*Attorney, Agent, or Firm*—Bierman and Muserlian

[57] ABSTRACT

The heart retractor for use in coronary bypass operations consists of a pair of long tapes, a short tape having an opening or a pair of short tapes and a couple of rings freely mounted thereon for forming an opening, and a longitudinal tape for connecting the long tapes and short tape or tapes in parallel with each other.

5 Claims, 6 Drawing Sheets

HEART RETRACTOR

BACKGROUND OF THE INVENTION

This invention relates to heart retractors, and more particularly to heart retractors for expeditious coronary bypass operations.

In coronary bypass operations, grafts have to be anastomosed to the anterior descending artery, the circumflex artery, and the posterior descending artery. The anterior descending artery lies on the front surface of the heart, and is easily accessible to the surgeon without particular help from surgical assistants or using any devices. The circumflex and posterior descending arteries, however, lie on the back surface of the heart. Therefore, to expose the circumflex artery to a field of view of the surgeon it is mandatory to lift the heart and rotate the heart about the axis of the inferior vena cava and the superior pulmonary veins. Likewise, to expose the posterior descending artery it is mandatory to lift the heart and rotate the heart in the direction of its apex.

Ordinarily a surgical assistant is employed to lift the heart by the assistant's hand. However, it is very difficult to keep the heart in a steady position. Furthermore, the myocardium in contact with the assistant's fingers may be damaged by pressure, avulsion, and premature rewarming.

It has heretofore been proposed to use a heart support device in the form of a net for coronary artery surgery which is formed of a plurality of flat cloth tapes crossing each other at right angles and stitched to provide a mesh with square openings. A fixation tape having free ends extending laterally in opposite direction is stitched to the narrow portion of the net-like support to secure it to the heart of the patient. One of the extending portions of the fixation tape is placed under the aorta and pulmonary artery, and the other portion is placed under the inferior vena cava and by pulling up the net, the heart is lifted and kept in a steady position. But this heart support device is found to be unsatisfactory in coronary bypass operations. In the way of surgery, the tape in the mesh prevents an obstructed view of the back surface of the heart and the coronary arteries to be grafted are covered by the portions of the net.

Another proposed method to lift the heart is the use of slings placed underneath the heart. However, with this method certain experience has to be developed before they can be handled with ease, and still it is often difficult to expose the coronary artery to be grafted.

OBJECTS OF THE INVENTION

In view of the foregoing, it is a main object of the present invention to provide an improved heart retractor for coronary artery surgery.

It is an object of the present invention to provide a heart retractor which can lift the heart safely and keep it in a steady position in the coronary bypass operation.

It is another object of the present invention to provide a heart retractor which can provide an unobstructed view of the back surface of the heart.

It is a further object of the present invention to provide a heart retractor which does not cause myocardial damage.

It is a still further object of the present invention to provide a heart retractor which can easily be handled by the surgeon without help from surgical assistants.

BRIEF DESCRIPTION OF THE DRAWING

The above and the other objects, features and advantages of the present invention will be more clearly understood when considered in conjunction with the following description and accompanying drawings in which.

DESCRIPTION OF THE PREFERRED EMBODIMENT

Figure 1:
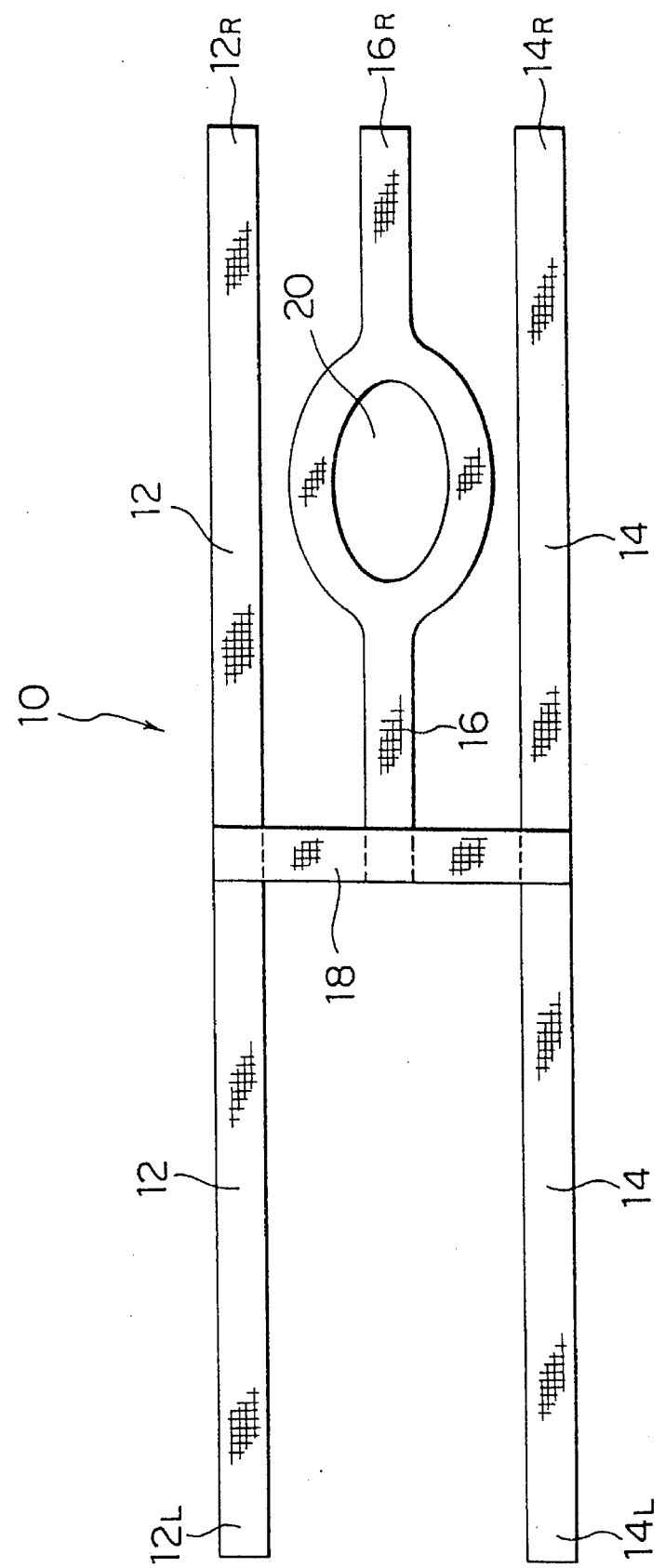
FIG. 1 is a plan view of a first embodiment of heart retractor according to the present invention.

Referring now in particular to the drawings, in FIG. 1, there is shown a first embodiment of a heart retractor according to the present invention. The heart retractor is generally designated by 10 consisting of a pair of laterally extending upper and lower long parallel tapes 12 and 14, a short tape 16 having an opening 20 in the central portion thereof and arranged between the long tapes 12 and 14 and a longitudinal tape 18 for connecting the tapes 12, 14 and 16.

The length of the short tape 16 is preferably about a half of the length of each of the long tapes 12 and 14. For example, the length of the long tape is about 80cm and the short tape is about 40 cm in length.

The central portion of each of the upper and lower long tapes 12 and 14 is fixed or stitched to each end of the longitudinal tape 18 and the free ends of each of the tapes 12 and 14 are extending laterally in opposite directions from the longitudinal tape 18. As shown in FIG. 1, the left end of the short tape 16 is fixed or stitched to the central portion of the longitudinal tape 18.

The opening 20 provided at the central portion of the short tape 16 serves to support the apex of the heart in a manner to be described hereinafter.

Figure 2:
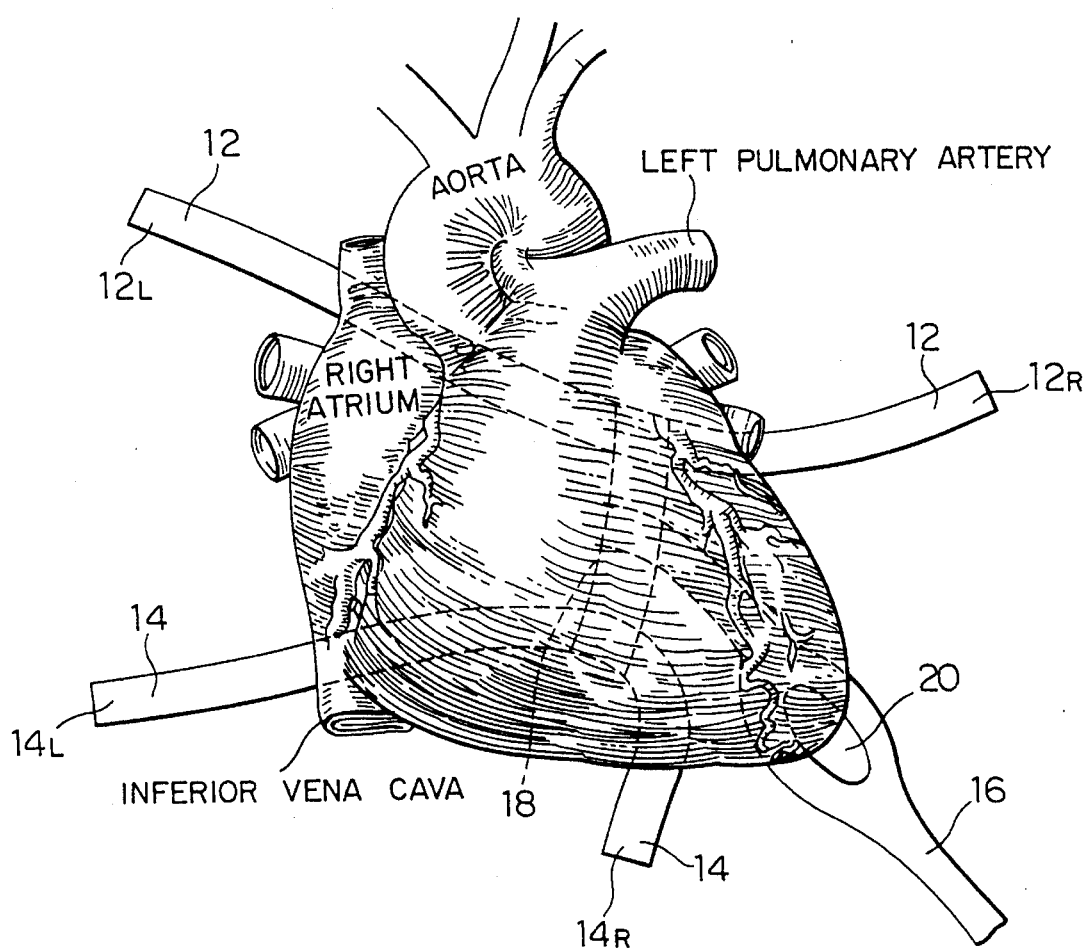
FIG. 2 is a schematic illustration showing the first embodiment of the heart retractor according to the present invention in which the retractor is placed behind the posterior of the heart of the patient and an opening in a short tape is faced to the apex of the heart.
Figure 3:
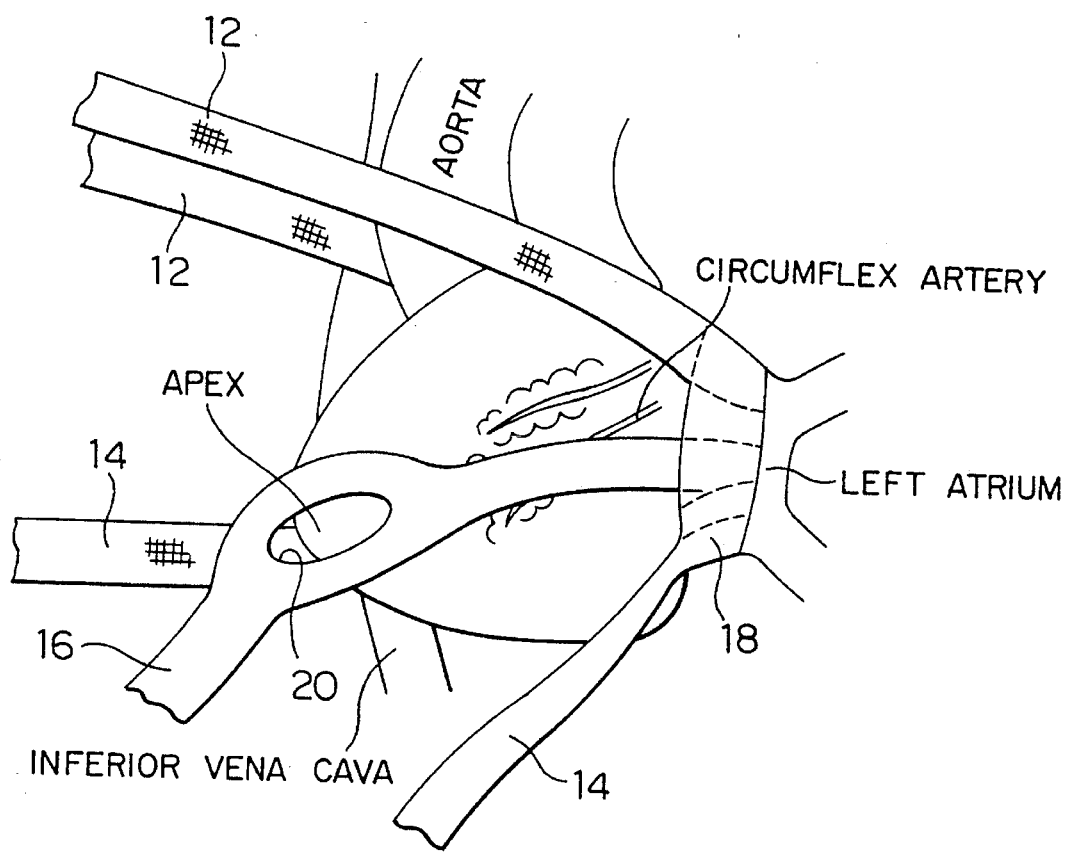
FIG. 3 is a schematic illustration showing that the heart is lifted by the first embodiment of the heart retractor according to the present invention for exposing the circumflex artery.
Figure 4:
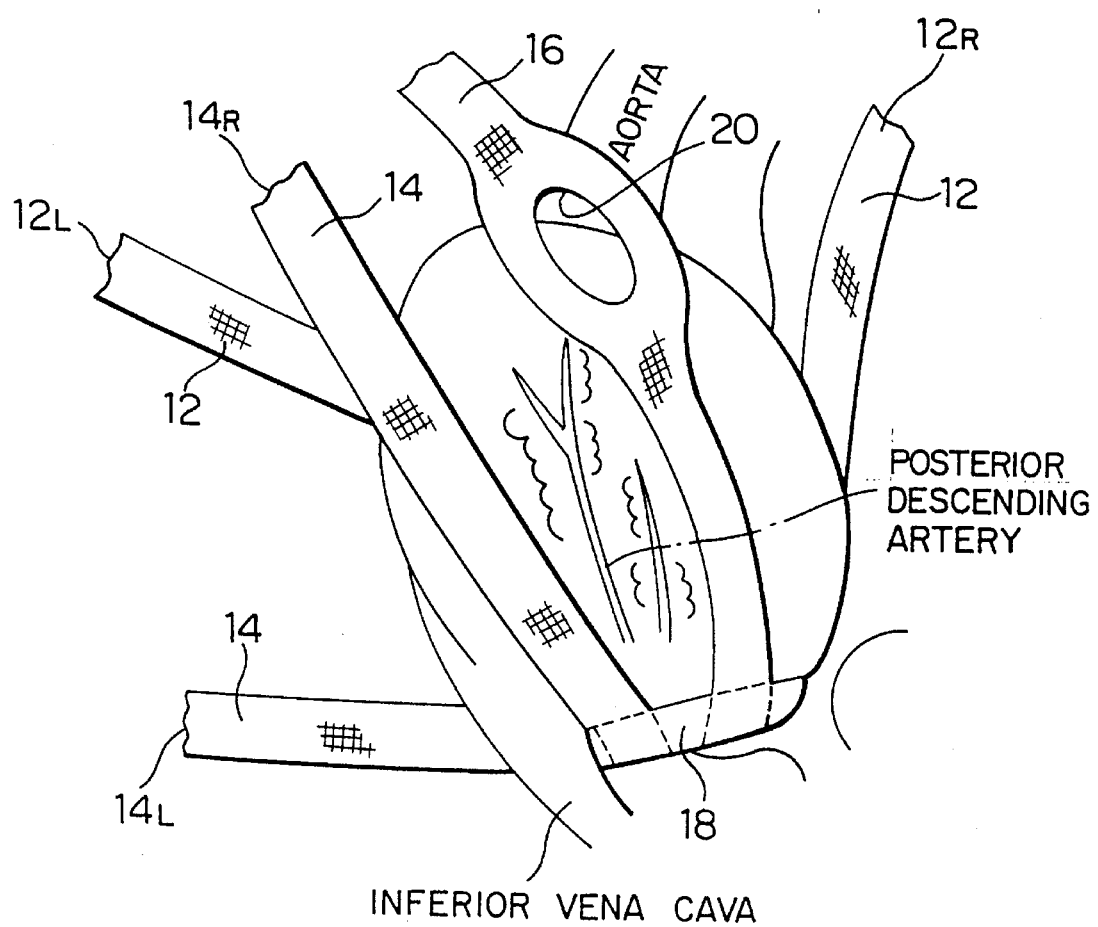
FIG. 4 is a schematic illustration showing that the heart is lifted by the first embodiment of the heart retractor according to the present invention for exposing the posterior artery.

In using the heart retractor 10 in coronary bypass operations, as shown in FIG. 2 through FIG. 4, the left side 12L of the upper long tape 12 is passed behind the aorta and pulmonary artery, and the left side 14L of the lower long tape 14 is passed behind the interior vena cava. Then they are pulled to the right so as to position the longitudinal tape 18 to the base of the heart. Thus the right side 12R, 14R of each of the long tapes 12 and 16R of the short tape 16 are positioned under the heart and the opening 20 in the short tape 16 is faced to the apex of the heart, as shown in FIG. 2. Accordingly, the opening 20 in the short tape 16 can receive and support the apex of the heart.

When the right side 12R, 16R of each of the upper tape 12 and the short tape 16 are pulled up to the right, the upper back surface of the heart is lifted and the circumflex artery is exposed to the surgeon's sight, as shown in FIG. 3.

On the other hand, when the short tape 16 and the right end of the lower long tape 14 are pulled up, the lower back surface of the heart is lifted and the surgeon can easily access the posterior descending artery.

The longitudinal tape 18 supports the base of the heart providing safety and stability for heart retraction. Moreover, since tapes 12, 14 and 16 can be moved freely, they can be positioned on any portion of the surface of the heart so that any coronary arteries to be grafted can always be exposed.

Figure 5:
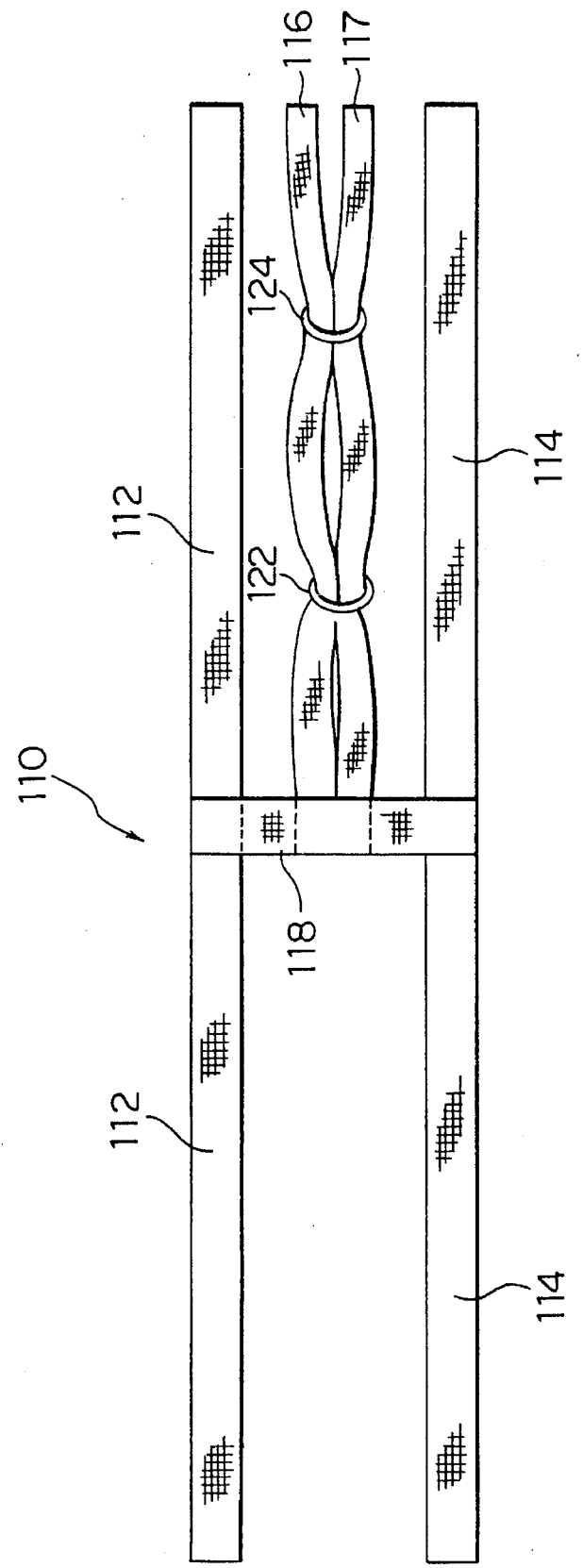
FIG. 5 is a plan view of a second embodiment of the heart retractor according to the present invention.

According to a second embodiment of the present invention, as shown in FIG. 5, a heart retractor 110 consists of a pair of the upper and lower long tapes 112 and 114, a pair of short tapes 116 and 117 arranged between the upper and lower long tapes 112 and 114, a longitudinal tape 118 for connecting the long tapes 112 and 114 and the short tapes 116 and 117 and a couple of rings 122 and 124 into which the short tapes 116 and 117 are freely inserted.

The central portion of each of the upper and lower long tapes 112 and 114 is fixed or stitched to each end of the longitudinal tape 118 and the left end of each of the short tapes 116 and 117 is fixed or stitched to the longitudinal tape 118 and free end of each of the tapes 112 and 114 are extending laterally in opposite direction from the vertical tape 118 which is placed in vertical direction with respect to each of the long tapes 112 and 114 and the left end of each of the short tapes 116 and 117 is fixed or stitched to the longitudinal tape 118 near the center thereof.

All of the tapes 12, 14, 16 and 18; or 112, 114, 116 117 and 118 are preferably made of a strong non-extensible fabric material and the rings 122 and 124 may be made of plastic material.

Figure 6:
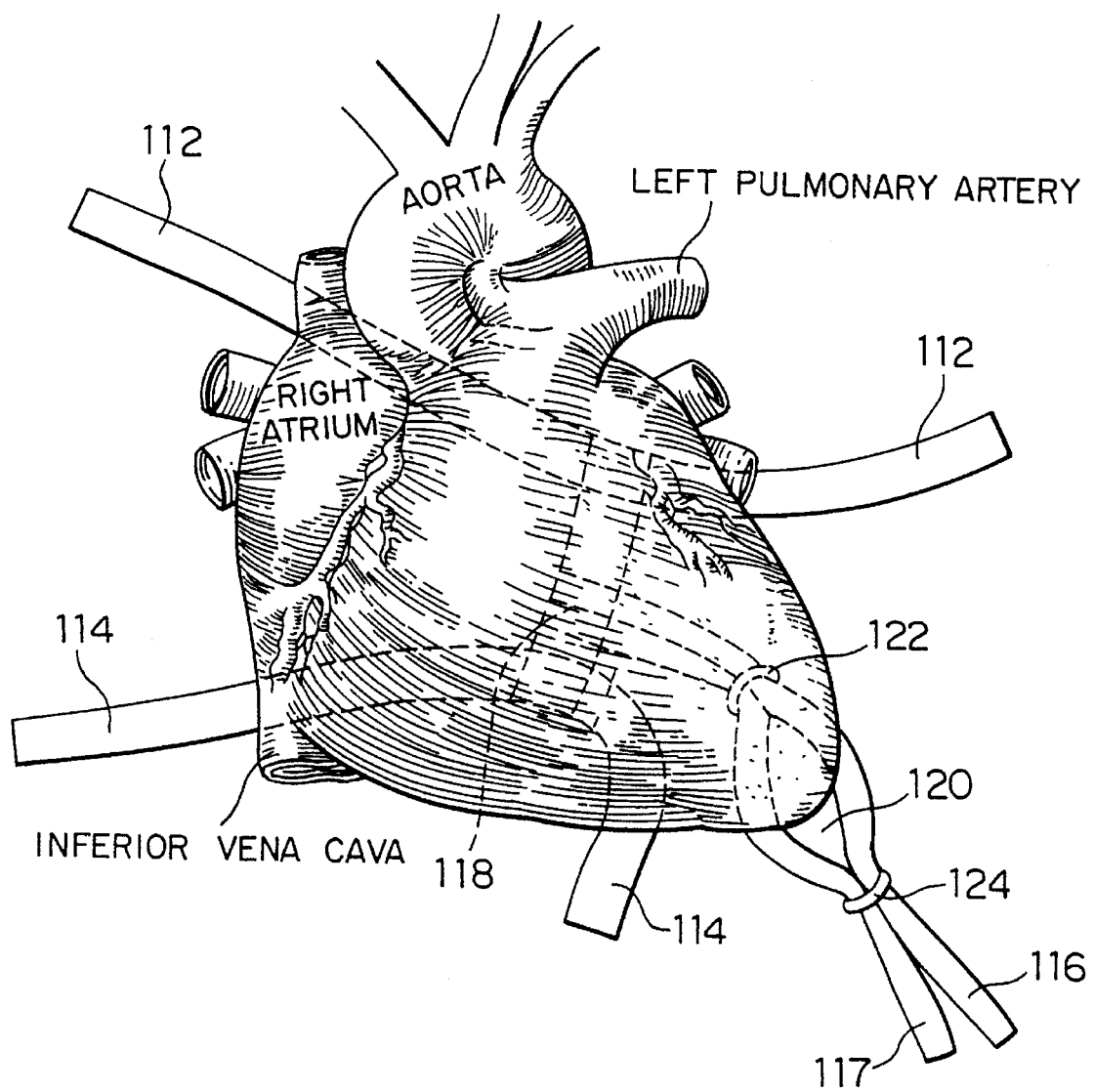
FIG. 6 is a schematic illustration showing that the heart is lifted by the second embodiment of the heart retractor in which an opening formed by a pair of short tapes and rings is Faced to the apex of the heart.

In the second embodiment of the present invention, the position of each of the rings 116 and 117 with respect to the short tapes 116 and 117 can be adjusted by the operator so that the opening 120 formed by tapes 116 and 117 comfortably accommodate the apex of the heart as shown in FIG. 6.

When the right half of tapes 112 and 114 and the right side of each of the short tapes are pulled up to the right, the upper back surface of the heart is lifted and the circumflex artery is exposed to surgeon's sight, as shown in FIG. 6. The apex of the heart is supported or secured in the opening 120 formed by short tapes 116 and 117 and two rings 122 and 124, which otherwise tends to fall off during surgical procedure.

On the other hand, when the short tapes 116 and 117 are pulled up, the lower back surface of the heart is lifted and the surgeon can have an easy access to the posterior descending artery.

The longitudinal tape 118 supports the base of the heart providing safety and stability for heart retraction. The two rings 122 and 124 mounted on the tapes 116 and 117 can be moved freely on the tapes so that the apex of the heart can always be gripped stabilized irrespective of the size of the heart. Moreover, since the tapes 112, and 114 can be moved freely, they can be positioned on any portion of the surface of the heart so that any coronary arteries to be grafted can always be exposed.

Thus, the present heart retractor holds the heart in steady position for coronary bypass operations and frees the assistant for other useful duties to aid the surgeon.

While I have herein described and disclosed preferred embodiments of the invention, it will nevertheless be understood that same is capable of modifications and changes within the scope of the appended claims.

What is claimed is:

1. A heart retractor for use in a coronary bypass operation comprising a pair of upper and lower parallel long tapes, a short tape having an opening arranged between the upper and lower tapes, and a longitudinal tape for connecting the upper and lower long tapes and the short tape in parallel with each other.

2. A heart retractor for use in a coronary bypass operation as claimed in claim 1 in which all of the long tapes, short tapes and longitudinal tape are made of a non-extensible fabric material.

3. A heart retractor for use in a coronary bypass operation as claimed in claim 1 in which the length of the short tape is about a half of the length of the long tape.

4. A heart retractor for use in a coronary bypass operation comprising a pair of upper and lower long tapes, a pair of short tapes arranged between the upper and lower long tapes, a couple of rings mounted on the pair of short tapes, and a longitudinal tape for connecting the upper and lower tapes and two short tapes in parallel with each other.

5. A heart retractor for use in a coronary bypass operation as claimed in claim 4 in which the two rings are made of plastic material.

* * * * *